United States Patent
Hillairet et al.

(10) Patent No.: US 8,399,582 B2
(45) Date of Patent: Mar. 19, 2013

(54) POLYMERISATION OF ETHYLENE AND ALPHA-OLEFINS WITH PYRIDINO-IMINOPHENOL COMPLEXES

(75) Inventors: Caroline Hillairet, Soignies (BE); Guillaume Michaud, Lille (FR); Sabine Sirol, Horrues (BE)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 708 days.

(21) Appl. No.: 12/298,331

(22) PCT Filed: Apr. 17, 2007

(86) PCT No.: PCT/EP2007/053720
§ 371 (c)(1),
(2), (4) Date: Feb. 11, 2010

(87) PCT Pub. No.: WO2007/122139
PCT Pub. Date: Nov. 1, 2007

(65) Prior Publication Data
US 2010/0160583 A1    Jun. 24, 2010

(30) Foreign Application Priority Data
Apr. 24, 2006  (EP) .................................. 06112984

(51) Int. Cl.
*C08F 4/64* (2006.01)
*C08F 4/76* (2006.01)
*C08F 4/52* (2006.01)

(52) U.S. Cl. ...... 526/161; 526/172; 526/169; 526/169.1; 526/348; 526/352; 526/351; 526/348.5

(58) Field of Classification Search .................. 502/113; 526/172, 161, 351, 352, 348.5
See application file for complete search history.

(56) References Cited

FOREIGN PATENT DOCUMENTS

EP   1 574 529 A1 * 9/2005
EP   1574529 A     9/2005

OTHER PUBLICATIONS

Duran et al., Anales de Quimica, Serie B: Quimica Inorganica y Quimica Analitica, 1988, 84, 60-64.*
Bacchi et al., Eur. J. Inorg. Chem., 2002, 2179-2187.*
Pachón et al., Inorg. Chim. Acta, 2004, 357, 3697-3702.*
Matsui, S. Et Al.: "FI Catalysts : Super active new ethylene polymerization catalysts" Catalysis Today, No. 66(1), 2001.

* cited by examiner

Primary Examiner — Rip A. Lee

(57) ABSTRACT

The present invention relates to the field of single site catalyst systems based on pyridine-iminophenol, pyridine-iminoalcohol or pyridine-iminoamine complexes and suitable for oligomerising or homo- or co-polymerising ethylene and alpha-olefins.

10 Claims, 3 Drawing Sheets

POLYMERISATION OF ETHYLENE AND ALPHA-OLEFINS WITH PYRIDINO-IMINOPHENOL COMPLEXES

CROSS-REFERENCE TO RELATED APPLICATIONS

This application claims the benefit of PCT/EP2007/053720, filed Apr. 17, 2007, which claims priority from EP 06112984.7, filed Apr. 24, 2006.

The present invention relates to the field of single site catalyst systems based on pyridine-iminophenol, pyridine-iminoalcohol or pyridine-iminoamine complexes and suitable for oligomerising or polymerising ethylene and alpha-olefins.

A multitude of catalyst systems available for polymerising or oligomerising ethylene and alpha-olefins exist, but there is a growing need for finding new systems capable of tailoring polymers with very specific properties. More and more post-metallocene catalyst components based on early or late transition metals from Groups 3 to 10 of the Periodic Table have recently been investigated such as for example those disclosed in Gibson and al. review (Gibson, V. C.; Spitzmesser, S. K., in Chem. Rev. 2003, 103, p. 283).

Pyridine-iminophenol derivatives are known and have been described for example by Ismet et al. (Ismet, K.; Fatma, M.; Dig Dem E. in Journal of Polymer Science: Part A: Polymer Chemistry, Vol. 42, 2717-2724, 2004) or by Asada et al. (Asada, H.; Hayashi, K.; Negoro, S.; Fujiwara, M.; Matsushita, T. in Inorganic Chemistry Communications 6, 193-196, 2003) or by Bacchi et al. (Bacchi, A.; Carcelli, M.; Pelizzi, C.; Pelizzi, G.; Pelagatti, P.; Ugolotti, S. in Eur. J. Inorg. Chem. 2179-2187, 2002), but corresponding complexes have never been described as catalysts for the polymerisation of olefins.

There is still a need to improve either the specificities or the performances of these systems.

It is an aim of this invention to provide new single site catalysts based on tridentate pyridine-iminophenol, pyridine-iminoalcohol or pyridine-iminoamine.

It is another aim of the present invention to provide active catalyst systems based on these catalyst components.

It is a further aim of the present invention to provide a process for polymerising or for oligomerising ethylene and alpha-olefins with these new catalyst systems.

Any one or more of these aims is fulfilled, at least partially, by the present invention.

Accordingly, the present invention discloses metallic complexes of formula I or of formula I'

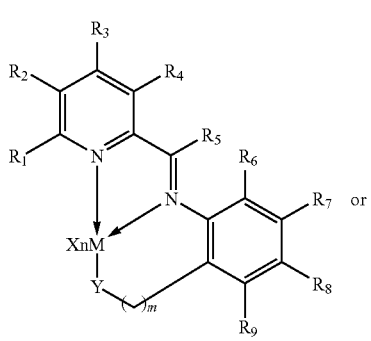

(I)

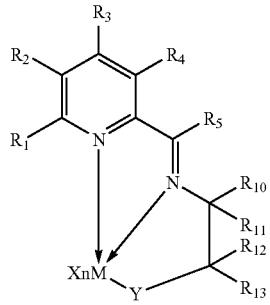

(I')

wherein $R_1$, $R_2$, $R_3$, $R_4$, $R_5$, $R_6$, $R_7$, $R_8$, $R_9$, $R_{10}$, $R_{11}$, $R_{12}$ and $R_{13}$ are each independently selected from hydrogen, unsubstituted or substituted hydrocarbyl having from 1 to 20 carbon atoms, or inert functional group. Two or more of those groups can themselves be linked together to form further ring or rings;

wherein M is a metal Group 3 to 10 of the Periodic Table;

wherein Y is O or NR*, with R* being alkyl or aryl group having from 1 to 12 carbon atoms;

wherein each X can be the same or different and is selected from halogen, substituted or unsubstituted hydrocarbyl having from 1 to 20 carbon atoms, substituted or unsubstituted aryloxy or alkoxy;

wherein m is zero or an integer from 1 to 3; and wherein (n+1) is the valence of M.

The metallic complex results from the complexation of a ligand of general formula II or of formula II' with metallic salt $MX_{n+1}$ in a solvent

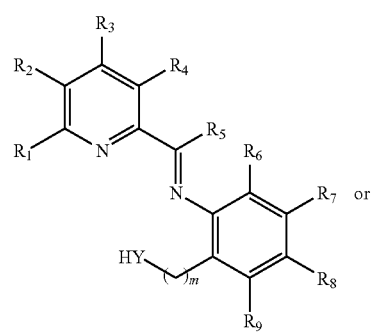

(II)

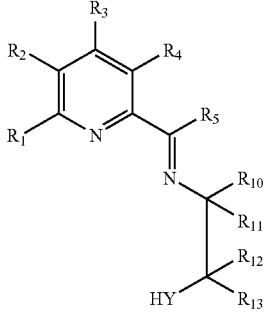

(II')

wherein $R_1$ to $R_{13}$ are as described hereabove.

Ligand of formula II or II' is the reaction product of carbonylated pyridine of formula III with compound of formula IV or IV',

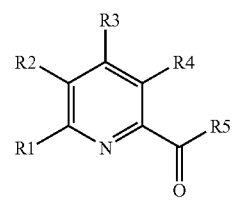

(III)

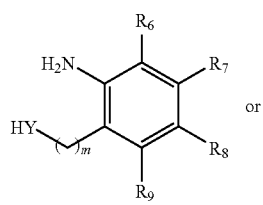

(IV)

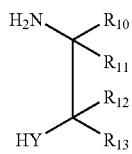

(IV')

wherein $R_1$ to $R_{13}$ are as described hereabove.

The reaction conditions are well known in the art.

By inert functional group, is meant a group, other than hydrocarbyl or substituted hydrocarbyl, that is inert under the complexation conditions to which the compound containing said group is subjected. They can be selected for example from halo, ester, ether, amino, imino, nitro, cyano, carboxyl, phosphate, phosphonite, phosphine, phosphinite, thioether and amide. Preferably, they are selected from halo, such as chloro, bromo, fluoro and iodo, or ether of formula —OR* wherein R* is unsubstituted or substituted hydrocarbyl. After metallation of the ligand, an inert functional group must not coordinate to the metal more strongly than the groups organised to coordinate to the metal and thereby displace the desired coordinating group.

In preferred embodiments according to the present invention, m is zero and $R_2$, $R_3$, $R_4$, $R_5$, $R_6$, $R_9$, $R_{10}$ and $R_{13}$ are hydrogen and $R_1$, $R_7$, $R_8$, $R_{11}$ and $R_{12}$ can each be independently selected from hydrogen, substituted or unsubstituted hydrocarbyl having from 1 to 20 carbon atoms, halogen, nitro or cyano groups.

In this description, substituted hydrocarbyls are defined as chains or links that may comprise one or more heteroatoms.

Some precursors for $R_1$ can advantageously be selected from aromatic or heteroaromatic boronic acids of formula

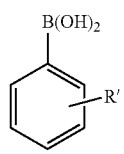

wherein each R' is independently selected from hydrogen or hydrocarbyl or inert functional group.

Other precursors for $R_1$ can be selected from any one of the following:

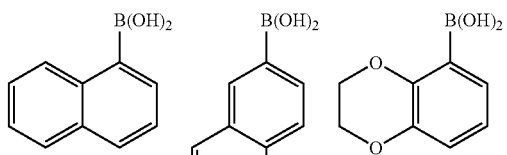

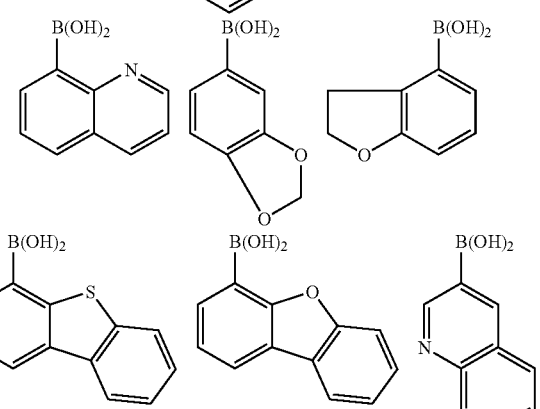

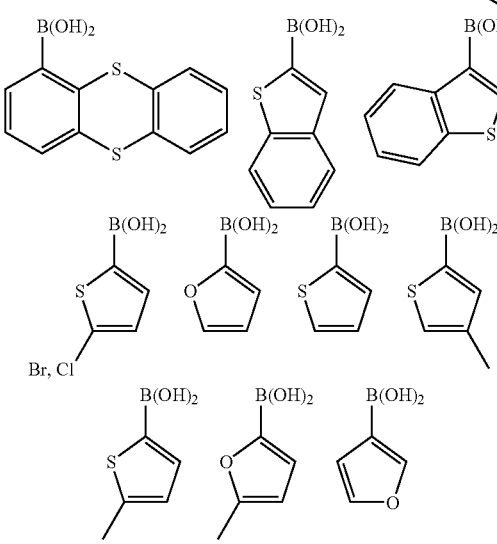

Preferably, $R_1$, $R_7$, $R_8$, $R_{11}$ and $R_{12}$ are each independently selected from hydrogen or substituted or unsubstituted alkyl or aryl groups or halogen.

The preferred alkyl groups are methyl and tert-butyl.

The preferred aryl groups are unsubstituted or substituted phenyl groups.

The preferred halogen is chlorine.

Preferably all three $R_1$, $R_7$ and $R_8$ are not hydrogen simultaneously.

More preferably either $R_7$ or $R_8$ is present, the other being hydrogen and $R_1$ is one of the preferred substituent groups or hydrogen.

Preferably M is Ti, Zr, Hf, V, Cr, Mn, Fe, Co, Ni, Pd or rare earths. More preferably, it is Ti, Cr, Fe or Zr.

Preferably X is halogen, more preferably it is chlorine.

The solvent may be selected from dichloromethane or tetrahydrofuran and the complexation reaction is carried out at room temperature or at reflux.

The present invention further discloses an active catalyst system comprising the single site catalyst component of formula I or I' and an activating agent having an ionising action.

Suitable activating agents are well known in the art. The activating agent can be an aluminium alkyl represented by formula $AlR^+_n X_{3-n}$ wherein $R^+$ is an alkyl having from 1 to 20 carbon atoms and X is a halogen. The preferred alkylating agents are triisobutyl aluminium (TIBAL) or triethyl aluminium (TEAL).

Alternatively, it can be aluminoxane and comprise oligomeric linear and/or cyclic alkyl aluminoxanes represented by formula

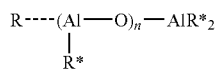

for oligomeric, linear aluminoxanes and by formula

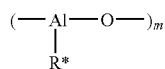

for oligomeric, cyclic aluminoxane,
wherein n is 1-40, preferably 10-20, m is 3-40, preferably 3-20 and R* is a $C_1$-$C_8$ alkyl group and preferably methyl.

Preferably, the activating agent is methylaluminoxane (MAO) or tetra-isobutyldialuminoxane (IBAO), more preferably, it is IBAO.

The amount of activating agent is selected to give an Al/M ratio of from 100 to 3000, preferably of from 500 to 2000. The amount of activating agent depends upon its nature: for IBAO the preferred Al/M ratio is of about 500, and for MAO, it is about 2000.

Suitable boron-containing activating agents may comprise a triphenylcarbenium boronate such as tetrakis-pentafluorophenyl-borato-triphenylcarbenium as described in EP-A-0427696, or those of the general formula $[L'-H]+[B\ Ar_1Ar_2X_3X_4]-$ as described in EP-A-0277004 (page 6, line 30 to page 7, line 7). The amount of boron-containing activating agent is selected to give B/M ratio of from 0.5 to 5, preferably of about 1.

In another embodiment, according to the present invention, the single site catalyst component of formula I may be deposited on a conventional support. Preferably, the conventional support is silica impregnated with MAO. Alternatively and preferably, it can be an activating support such as fluorinated alumina silica.

The present invention further discloses a method for preparing an active catalyst system that comprises the steps of:
a) providing a ligand of formula II;
b) complexing the ligand of step a) with a metallic salt $MX_{n+1}$ in a solvent;
c) retrieving catalyst component I;
d) activating with an activating agent having an ionising action;
e) optionally adding a cocatalyst;
f) retrieving an active oligomerisation or polymerisation catalyst system.

Alternatively, in step d) catalyst component I is deposited on a support impregnated with an activating agent or on an activating support containing fluor.

The cocatalyst may be selected from triethylaluminium, triisobutylaluminum, tris-n-octylaluminium, tetraisobutyldialuminoxane or diethyl zinc.

The active catalyst system is used in the oligomerisation and in the polymerisation of ethylene and alpha-olefins.

The present invention discloses a method for the oligomerisation or the homo- or co-polymerisation of ethylene and alpha-olefins that comprises the steps of:
a) injecting the active catalyst system into the reactor; and
b) injecting the monomer and optional comonomer either before or after or simultaneously with step a);
c) maintaining under polymerisation conditions;
d) retrieving the oligomers and/or polymer.

The pressure in the reactor can vary from 0.5 to 50 bars, preferably from 5 to 25 bars.

The polymerisation temperature can range from 10 to 100° C., preferably from 50 to 85° C.

Preferably the monomer and optional comonomer are selected from ethylene, propylene or 1-hexene.

In another preferred embodiment according to the present invention, the optional comonomer is a polar functionalised alpha-olefin.

LIST OF FIGURES

EXAMPLES

Figure 1:
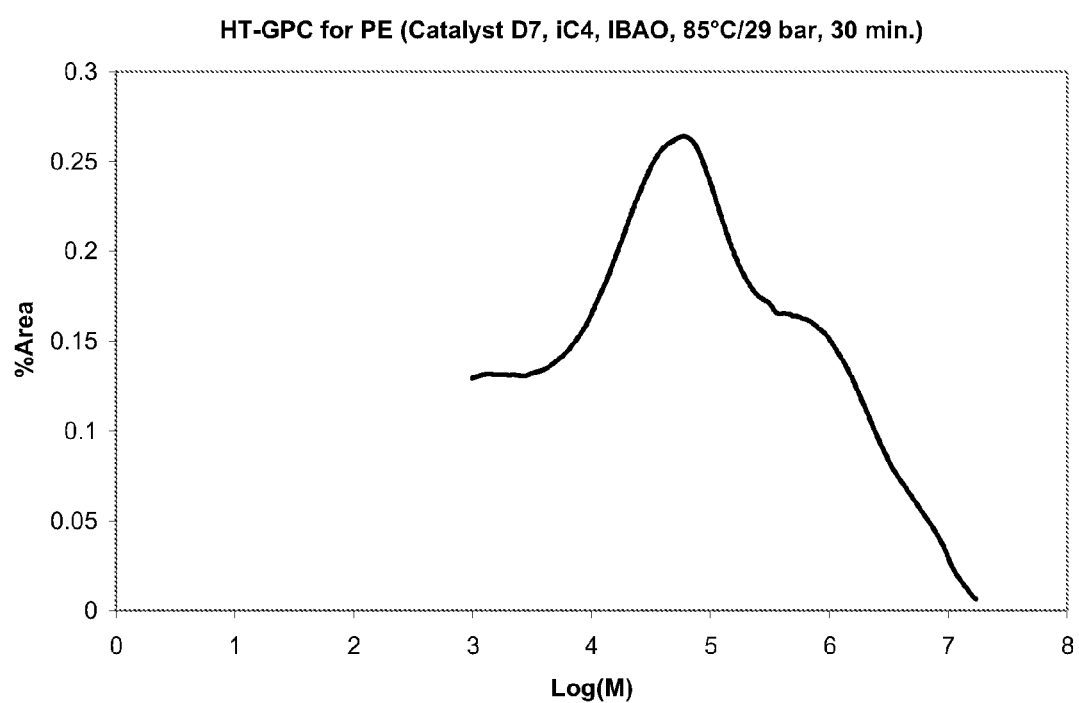
FIG. 1 represents the Gel Permeation Chromatography (GPC) curve of the polyethylene resin obtained with catalyst D7 activated with IBAO, with iC4 as solvent, at a temperature of 85° C., under an ethylene pressure of 29 bars and after a polymerisation time of 30 minutes.

All reactions were performed using standard Schlenk techniques or in an argon-filled glove-box. The starting materials and reagents, purchased from commercial suppliers, were used without purification. All the solvents were dried and distilled before use either over sodium and benzophenone for toluene, pentane and THF, or over $CaH_2$ for ethanol. $^1H$, $^{13}C$ and $^{31}P$ NMR spectra were recorded on a Bruker Advance300 apparatus.

Preparation of Ligands

I. Precursors

Synthesis of precursor
[6-phenyl]-2-pyridinecarboxaldehyde (A)

192 mg (1 mmol) of 6-bromo-2-pyridinecarboxaldehyde and 152 mg (1.2 mmol) of phenylboronic acid were dissolved in 10 mL of tetrahydrofuran (THF). 1 ml (1 mmol) of $Na_2CO_3$ in aqueous solution (1M) and 8 mg (0.7%) of $Pd(PPh_3)_4$ were added. The reaction mixture was heated during 45 min, at a temperature of 130° C. in a micro-wave reactor. The solution was filtered on paper, 10 ml of AcOEt were added and the organic phase was successively washed with NaHCO$_3$, with H$_2$O and with an aqueous solution of NaCl. The organic phase was dried over MgSO$_4$, filtered and evaporated to dryness. After a chromatography on silica gel (Pentane/Et$_{2O}$, 1/1), 136 mg of aldehyde A were obtained as colourless oil with a yield of 74%.

A $^1$H NMR (300 MHz, CDCl$_3$) δ (ppm): 10.17 (s, 1H), 8.11 (d, J=6 Hz, 2H), 7.89 (m, 3H), 7.49 (m, 3H)

$^{13}$C{$^1$H} NMR (75 MHz, CDCl$_3$) δ (ppm): 114.5, 119.2, 121.8, 123.7, 124.4, 132.5, 132.8, 147.5, 188.7.

Synthesis of precursor [6-(2-phenyl)phenyl]-2-pyridinecarboxaldehyde (B)

Precursor (B) was prepared following the same procedure as that used to prepare precursor (A) except that 238 mg (1.2 mmol) of (2-phenyl)phenylboronic acid were used as reagent. 255 mg of precursor (B) were obtained as colourless oil with a yield of 98%.

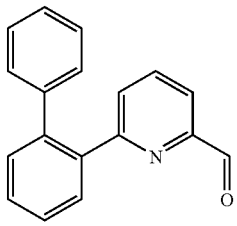

B $^1$H NMR (300 MHz, CDCl$_3$) δ (ppm): 10.09 (s, 1H), 7.79 (d, J=6 Hz, 2H), 7.52 (m, 4H), 7.25 (m, 3H), 7.15 (m, 3H)

$^{13}$C{$^1$H} NMR (75 MHz, CDCl$_3$) δ (ppm): 119.2, 127.0, 127.9, 128.2, 129.1, 129.5, 129.7, 130.7, 135.0, 136.1, 138.2, 140.9, 152.5, 159.9, 193.7.

Synthesis of precursor [6-(2,6-dimethylphenyl)]-2-pyridinecarboxaldehyde (C)

Precursor (C) was prepared following the same procedure as that used to prepare precursor (A) except that 180 mg (1.2 mmol) of 2,6-(dimethyl)phenylboronic acid were used as reagent. 200 mg of precursor (C) were obtained as colourless oil with a yield of 95%.

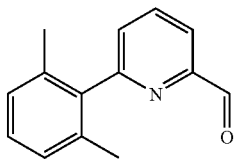

C $^1$H NMR (300 MHz, CDCl$_3$) δ (ppm): 10.13 (s, 1H), 7.96 (d, J=6 Hz, 2H), 7.48 (m, 1H), 7.25 (m, 1H), 6.99 (d, J=6 Hz, 2H), 2.06 (s, 6H)

$^{13}$C{$^1$H} NMR (75 MHz, CDCl$_3$) δ (ppm): 15.0, 114.3, 121.5, 122.6, 123.2, 123.7, 132.1, 147.6, 188.6.

Synthesis of precursor [6-naphthyl]-2-pyridinecarboxaldehyde (D)

Precursor (D) was prepared following the same procedure as that used to prepare precursor (A) except that 206 mg (1.2 mmol) of 2-naphthylboronic acid were used as reagent. 190 mg of precursor (D) were obtained as colourless oil with a yield of 82%.

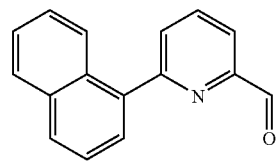

D $^1$H NMR (300 MHz, CDCl$_3$) δ (ppm): 10.21 (s, 1H), 8.01 (m, 5H), 7.80 (d, J=6 Hz, 1H), 7.55 (m, 4H)

$^{13}$C{$^1$H} NMR (75 MHz, CDCl$_3$) δ (ppm): 114.6, 120.0, 120.1, 120.9, 121.6, 122.5, 123.3, 124.0, 124.3, 128.7, 132.0, 132.3, 148.0, 154.7, 188.6.

Synthesis of precursor [6-(2-methoxyphenyl)]-2-pyridinecarboxaldehyde (E)

Precursor (E) was prepared following the same procedure as that used to prepare precursor (A) except that 376 mg (2.4 mmol) of 2-methylphenylboronic acid were used as reagent. 425 mg of precursor (E) were obtained as colourless oil with a yield of 98%.

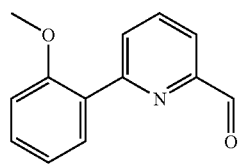

E $^1$H NMR (300 MHz, CDCl$_3$) δ (ppm): 3.90 (s, 3H), 7.06 (d, J=2.1 Hz, 1H), 7.15 (t, J=2.0 Hz, 1H), 7.45 (dt, J=2 Hz and J=0.4 Hz, 1H), 7.91 (m, 3H), 8.11 (dd, J=1.6 Hz and J=0.7 Hz, 1'-1), 10.2 (s, 1H).

Synthesis of precursor [6-(quinolin-8-yl)]-2-pyridinecarboxaldehyde (F)

Precursor (F) was prepared following the same procedure as that used to prepare precursor (A) except that 216 mg (1.2 mmol) of 8-quinolineboronic acid were used as reagent. 232 mg of precursor (F) were obtained as pale yellow solid with a yield of 99%.

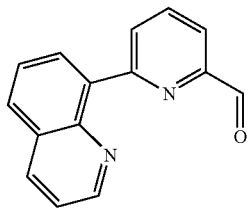

F $^1$H NMR (300 MHz, CDCl$_3$) δ (ppm): 7.49 (dd, J=2.0 Hz and J=1.0 Hz, 1H), 7.74 (t, J=2.0 Hz, 1H), 7.96 (d, J=2.0 Hz, 1H), 8.01 (m, 2H), 8.27 (d, J=2.0 Hz, 2H), 8.41 (m, 1H), 8.98 (dd, J=1.0 Hz and J=0.4 Hz, 1H), 10.22 (s, 1H).

Synthesis of precursor [6-(2-trifluoromethyl)]-2-pyridinecarboxaldehyde (G)

Precursor (G) was prepared following the same procedure as that used to prepare precursor (A) except that 470 mg (2.4 mmol) of 2-trifluoromethylphenylboronic acid were used as reagent. 477 mg of precursor (G) were obtained as orange oil with a yield of 95%.

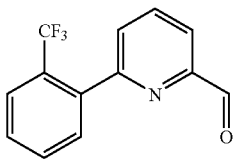

G $^1$H NMR (300 MHz, CDCl$_3$) δ (ppm): 7.57 (dt, J=2.0 Hz and J=0.4 Hz, 2H), 7.67 (dd, J=1.6 Hz and J=0.4 Hz, 2H), 7.83 (d, J=1.8 Hz, 1H), 7.99 (m, 2H), 10.12 (s, 1H).

Synthesis of precursor [6-(4-dibenzofuran)]-2-pyridinecarboxaldehyde (H)

Precursor (H) was prepared following the same procedure as that used to prepare precursor (A) except that 524 mg (2.4 mmol) of dibenzofuran-4-boronic acid were used as reagent. 540 mg of precursor (H) were obtained as pale yellow solid with a Yield of 99%.

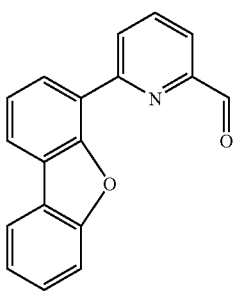

H $^1$H NMR (300 MHz, CDCl$_3$) δ (ppm): 7.42 (t, J=2.01 Hz, 1H), 7.54 (q, J=1.9 Hz, 2H), 7.67 (d, J=1.91 Hz, 1H), 8.00 (t, J=2.01 Hz, 2H), 8.06 (m, 2H), 8.49 (d, J=2.0 Hz, 1H), 8.73 (d, J=2.0 Hz, 1H), 10.24 (s, 1H).

II. Ligands

Synthesis of ligand 2[(2-pyridyl)-methylimino]-phenol (L1)

200 μl (2 mmol) of 2-pyridinecarboxaldehyde (reagent 1) and 220 mg (2 mmol) of 2-aminophenol (reagent 2) were dissolved in 10 mL of dry ethanol. One drop of glacial acetic acid was added and the reaction mixture was stirred during 12 h. The solution was filtered on paper and the filtrate was evaporated to dryness. After a chromatography on silica gel (CH$_2$Cl$_2$, 100 ml then AcOEt 200 ml), 394 mg of ligand L1 were obtained as orange solid with a yield of 100%.

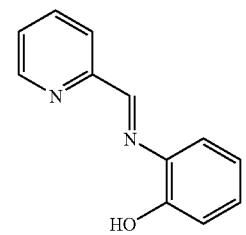

L1

$^1$H NMR (300 MHz, CDCl$_3$) δ (ppm): 8.83 (s, 1H), 8.72 (d, J=6 Hz, 1H), 8.17 (d, J=9 Hz, 1H), 7.83 (t, J=6 Hz, 1H), 7.38 (m, 2H), 7.22 (d, J=9 Hz, 1H), 7.03 (d, J=9 Hz, 1H), 6.95 (t, J=9 Hz, 1H)

$^{13}$C{$^1$H} NMR (75 MHz, CDCl$_3$) δ (ppm): 115.4, 116.1, 120.2, 121.8, 125.2, 129.9, 134.5, 136.8, 149.7, 152.8, 154.1, 156.7.

Synthesis of ligand 2-phenyl-2-(pyridylmethyleneamino)ethanol (L2)

Ligand L2 was prepared following the same procedure as that used to prepare ligand L1 except that 200 μl (2 mmol) of 2-phenylglycinol were used as reagent 2. 196 mg of ligand L2 were obtained yellow oil with a yield of 43%.

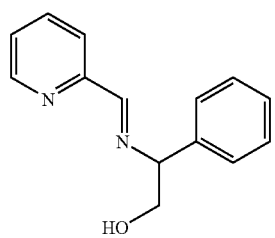

L2

$^1$H NMR (300 MHz, CD$_2$Cl$_2$) δ (ppm): 8.58 (m, 1H), 8.44 (s, 1H), 8.00 (d, J=9 Hz, 1H), 7.70 (t, J=9 Hz, 1H), 7.40-7.26 (m, 6H), 4.53 (m, 1H), 3.90-3.63 (m, 2H), 2.90 (bs, 1H).

Synthesis of ligand 2-[(2-pyridyl)-methylimino]-4-methyl-phenol (L3)

Ligand L3 was prepared following the same procedure as that used to prepare ligand L1 except that 635 mg (5 mmol) of 2-amino-4-methyl-phenol were used as reagent 2. 850 mg of ligand L3 were obtained as yellow-green solid with a yield of 80%.

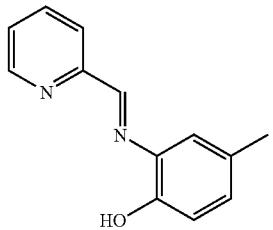

L3

$^1$H NMR (300 MHz, CDCl$_3$) δ (ppm): 8.82 (s, 1H), 8.73 (d, J=6 Hz, 1H), 8.19 (d, J=9 Hz, 1H), 7.83 (t, J=6 Hz, 1H), 7.40 (m, 1H), 7.20 (s, 1H), 7.05 (d, J=9 Hz, 1H), 6.92 (d, J=9 Hz, 1H), 2.31 (s, 3H)

$^{13}$C{$^1$H} NMR (75 MHz, CD$_2$Cl$_2$) δ (ppm): 21.0, 115.5, 117.4, 122.0, 125.7, 130.1, 130.9, 134.9, 137.1, 150.3, 151.1, 155.0, 157.8.

Synthesis of ligand
2-[(2-pyridyl)-methylimino]-5-methyl-phenol (L4)

Ligand L4 was prepared following the same procedure as that used to prepare ligand L1 except that 628 mg (5 mmol) of 2-amino-5-methyl-phenol were used as reagent 2. 928 mg of ligand L4 were obtained as light brown solid with a yield of 87%.

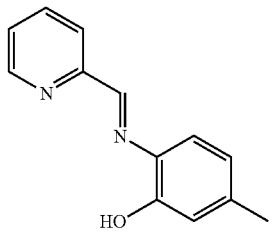

L4

$^1$H NMR (300 MHz, CDCl$_3$) δ (ppm): 8.81 (s, 1H), 8.71 (d, J=6 Hz, 1H), 8.18 (d, J=9 Hz, 1H), 7.81 (t, J=6 Hz, 1H), 7.37 (m, 1H), 7.31 (d, J=9 Hz, 1H), 6.86 (s, 1H), 6.73 (d, J=9 Hz, 1H), 2.35 (s, 3H)

$^{13}$C{$^1$H} NMR (75 MHz, CD$_2$Cl$_2$) δ (ppm): 21.8, 116.2, 116.4, 121.6, 122.0, 125.6, 132.7, 137.2, 141.2, 150.3, 153.3, 155.1, 156.6.

Synthesis of ligand
2-[(2-pyridyl)-methylimino]-4-tertbutyl-phenol (L5)

Ligand L5 was prepared following the same procedure as that used to prepare ligand L1 except that 852 mg (5 mmol) of 2-amino-4-tertbutyl-phenol were used as reagent 2. 1353 mg of ligand L5 were obtained as yellow-green solid with a yield of 99%.

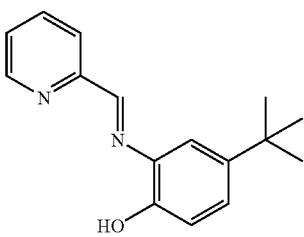

L5

$^1$H NMR (300 MHz, CDCl$_3$) δ (ppm): 8.88 (s, 1H), 8.72 (d, J=6 Hz, 1H), 8.21 (d, J=9 Hz, 1H), 7.83 (t, J=6 Hz, 1H), 7.43 (d, J=6 Hz, 1H), 7.39 (m, 1H), 7.30 (d, J=9 Hz, 1H), 7.12 (bs, 1H), 6.97 (d, J=9 Hz, 1H), 1.33 (s, 9H)

$^{13}$C{$^1$H} NMR (75 MHz, CD$_2$Cl$_2$) δ (ppm): 31.8, 34.8, 113.7, 115.1, 121.9, 125.7, 127.5, 129.3, 134.5, 137.1, 143.8, 150.3, 150.9, 157.8.

Synthesis of ligand
2-[(2-pyridyl)-methylimino]-4-phenyl-phenol (L6)

Ligand L6 was prepared following the same procedure as that used to prepare ligand L1 except that 1029 mg (5 mmol) of 2-amino-3-methyl-phenol were used as reagent 2. 1355 mg of ligand L6 were obtained as brown-red solid with a yield of 99%.

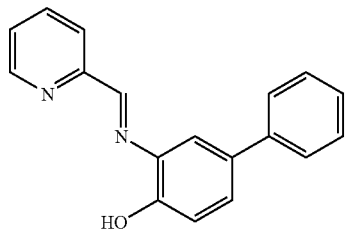

L6

$^1$H NMR (300 MHz, CDCl$_3$) δ (ppm): 8.94 (s, 1H), 8.81 (d, J=6 Hz, 1H), 8.10 (d, J=9 Hz, 1H), 7.87 (t, J=6 Hz, 1H), 7.63-7.31 (m, 8H), 7.12 (d, J=9 Hz, 1H)

$^{13}$C{$^1$H} NMR (75 MHz, CD$_2$Cl$_2$) b (ppm): 115.5, 116.1, 122.3, 125.9, 127.2, 127.4, 129.0, 129.3, 134.0, 135.5, 137.3, 141.1, 150.4, 152.8, 154.8, 158.5.

Synthesis of ligand
2-[(2-pyridyl)-methylimino]-4-chloro-phenol (L7)

Ligand L7 was prepared following the same procedure as that used to prepare ligand L1 except that 740 mg (5 mmol) of 2-amino-4-chloro-phenol were used as reagent 2. 1203 mg of ligand L7 were obtained as brown solid with a yield of 99%.

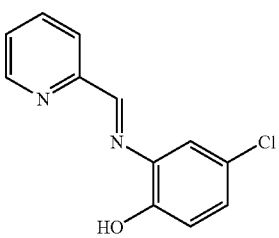

L7

$^1$H NMR (300 MHz, CDCl$_3$) δ (ppm): 8.79 (s, 1H), 8.74 (d, J=6 Hz, 1H), 8.18 (d, J=9 Hz, 1H), 7.83 (t, J=6 Hz, 1H), 7.43 (m, 1H), 7.38 (d, J=6 Hz, 1H), 7.21 (dd, J=2 Hz, J=9 Hz, 1H), 6.98 (d, J=9 Hz, 1H)

$^{13}$C{$^1$H} NMR (75 MHz, CDCl$_3$) δ (ppm): 116.3; 116.4; 121.8; 125.1; 125.5; 129.4; 135.1; 136.6; 149.8; 151.1; 153.7; 158.3.

Synthesis of ligand 2-[(2-pyridyl)-methylimino]-4-nitro-phenol (L8)

Ligand L8 was prepared following the same procedure as that used to prepare ligand L1 except that 803 mg (5 mmol) of 2-amino-4-nitro-phenol were used as reagent 2. 1029 mg of ligand L8 were obtained as beige solid with a yield of 85%.

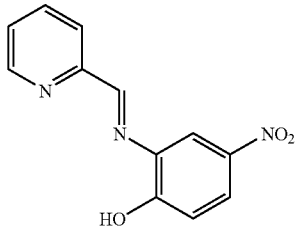

L8

$^1$H NMR (300 MHz, CD$_2$Cl$_2$) δ (ppm): 8.93 (s, 1H), 8.73 (d, J=6 Hz, 1H), 8.34 (d, J=6 Hz, 1H), 8.21 (d, J=9 Hz, 1H), 8.14 (dd, J=9 Hz, 1H), 7.86 (t, J=9 Hz, 1H), 7.44 (m, 1H), 7.09 (d, J=9 Hz, 1H).

Synthesis of ligand 2-[(2-(6-phenyl)-pyridyl)-methylimino]-phenol (L9)

Ligand L9 was prepared following the same procedure as that used to prepare ligand L1 except that 184 mg (1 mmol) of precursor A were used as reagent 1. 261 mg of ligand L9 were obtained as yellow solid with a yield of 95%.

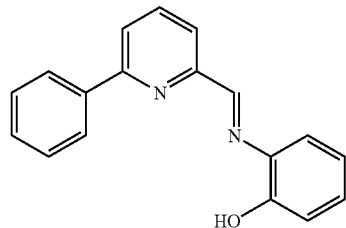

L9

Synthesis of ligand 2-[(2-(6-(2,6-dimethylphenyl)-pyridyl)-methylimino]-phenol (L10)

Ligand L10 was prepared following the same procedure as that used to prepare ligand L1 except that 99 mg (1 mmol) of precursor C were used as reagent 1. 261 mg of ligand L10 were obtained as yellow solid with a yield of 95%.

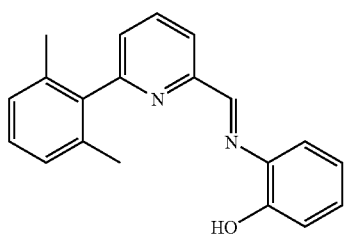

L10

Synthesis of ligand 2-[(2-(6-naphtyl)-pyridyl)-methylimino]-phenol (L11)

Ligand L11 was prepared following the same procedure as that used to prepare ligand L1 except that 233 mg (1 mmol) of precursor D were used as reagent 1. 149 mg of ligand L11 were obtained as yellow solid with a yield of 46%.

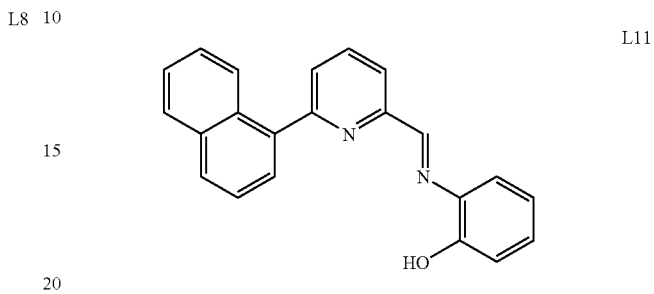

L11

$^1$H NMR (300 MHz, CD$_2$Cl$_2$) δ (ppm): 8.92 (s, 1H), 8.28 (d, J=6 Hz, 1H), 8.10 (d, J=6 Hz, 1H), 7.96 (m, 3H), 7.68-7.41 (m, 7H), 7.23 (t, J=6 Hz, 1H), 7.01 (d, J=6 Hz, 1H), 6.88 (t, J=6 Hz, 1H)

$^{13}$C{$^1$H} NMR (75 MHz, CD$_2$Cl$_2$) δ (ppm): 115.7, 116.9, 120.2, 120.8, 125.9, 126.1, 126.5, 127.0, 127.2, 128.1, 128.9, 129.6, 130.4, 134.5, 137.7, 154.7, 158.6.

Synthesis of ligand 2-[6-(2-phenyl)phenyl-2-pyridyl)-methylimino]-phenol (L12)

Ligand L12 was prepared following the same procedure as that used to prepare ligand L1 except that 259 mg (1 mmol) of precursor B were used as reagent 1. 266 mg of ligand L12 were obtained as yellow solid with a yield of 67%.

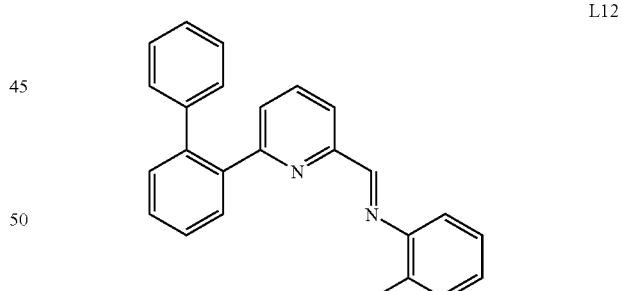

L12

$^1$H NMR (300 MHz, CDCl$_3$) δ (ppm): 8.81 (s, 1H), 8.03 (d, J=6 Hz, 1H), 7.71-7.31 (m, 7H), 7.21-6.92 (m, 8H).

Synthesis of ligand 2-[2-(6-phenyl)-pyridyl)-methylimino]-4-nitro-phenol (L13)

Ligand L13 was prepared following the same procedure as that used to prepare ligand L1 except that 183 mg (1 mmol) of precursor A were used as reagent 1 and 154 mg (1 mmol) of 2-amino-4-nitrophenol as reagent 2. 240 mg of ligand L13 were obtained as yellow solid with a yield of 75%.

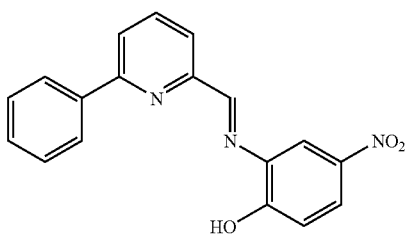

L13

$^1$H NMR 300 MHz, CD$_2$Cl$_2$) δ (ppm): 9.02 (s, 1H), 8.38 (d, J=3 Hz, 1H), 8.12 (d, J=9 Hz, 2H), 8.08 (d, J=9 Hz; 2H), 7.90 (m, 2H), 7.53-7.42 (m, 3H), 7.10 (d, J=9 Hz, 1H).

Synthesis of ligand 2-[(2-(6-(2,6-dimethylphenyl)-pyridyl)-methylimino]-4-nitro-phenol (L14)

Ligand L14 was prepared following the same procedure as that used to prepare ligand L1 except that 211 mg (1 mmol) of precursor C were used as reagent 1 and 154 mg (1 mmol) of 2-amino-4-nitrophenol as reagent 2. 108 mg of ligand L14 were obtained as yellow solid with a yield of 31%.

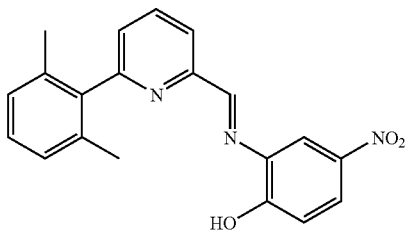

L14

$^1$H NMR (300 MHz, CD$_2$Cl$_2$) δ (ppm): 8.92 (s, 1H), 8.31 (d, J=3 Hz, 1H), 8.12 (d, J=9 Hz, 1H), 8.05-7.88 (m, 2H), 7.40 (d, J=9 Hz, 1H), 7.20 (t, J=9 Hz, 1H), 7.10 (d, J=9 Hz, 2H), 6.90 (d, J=9 Hz, 1H), 2.03 (s, 6H).

Synthesis of ligand 2-[(2-(6-naphthyl)-pyridyl)-methylimino]-4-nitro-phenol (L15)

Ligand L15 was prepared following the same procedure as that used to prepare ligand L1 except that 233 mg (1 mmol) of precursor D were used as reagent 1 and 154 mg (1 mmol) of 2-amino-4-nitrophenol as reagent 2. 320 mg of ligand L15 were obtained as yellow solid with a yield of 86%.

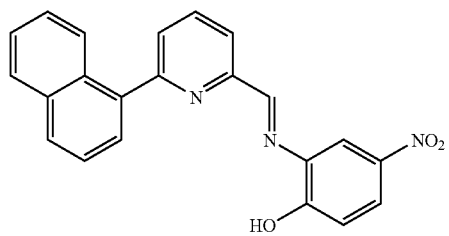

L15

$^1$H NMR (300 MHz, CD$_2$Cl$_2$) δ (ppm): 9.02 (s, 1H), 8.35 (d, J=3 Hz, 1H), 8.26 (d, J=9 Hz, 1H), 8.16-8.04 (m, 2H), 7.98 (t, J=9 Hz, 1H), 7.96-7.92 (m, 2H), 7.72 (d, J=9 Hz, 1H), 7.63-7.48 (m, 4H), 7.09 (d, J=9 Hz, 1H), 2.03 (s, 6H).

Synthesis of ligand 2-[(2-(6-(2-phenyl)phenyl)-pyridyl)-methylimino]-4-nitro-phenol (L16)

Ligand L16 was prepared following the same procedure as that used to prepare ligand L1 except that 259 mg (1 mmol) of precursor B were used as reagent 1 and 154 mg (1 mmol) of 2-amino-4-nitrophenol as reagent 2. 390 mg of ligand L16 were obtained as yellow solid with a yield of 98%.

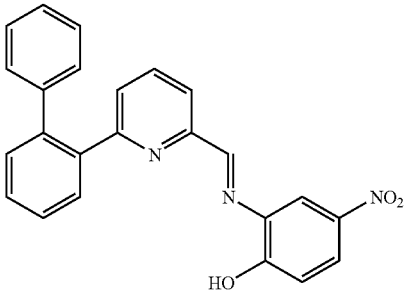

L16

$^1$H NMR (300 MHz, CD$_2$Cl$_2$) δ (ppm): 8.90 (s, 1H), 8.32 (s, 1H), 8.14 (m, 1H), 8.01 (d, J=9 Hz, 1H), 7.73 (m, 1H), 7.55-7.46 (m, 5H), 7.24-7.04 (m, 6H).

Synthesis of ligand 2-[2-(6-methylpyridyl)-methylimino]-phenol (L17)

Ligand L17 was prepared following the same procedure as that used to prepare ligand L1 except that 247 mg (1 mmol) of 2 picoline-6-carboxaldehyde were used as reagent 1 and 220 mg (2 mmol) of 2-aminophenol as reagent 2. 328 mg of ligand L17 were obtained as yellow solid with a yield of 77%.

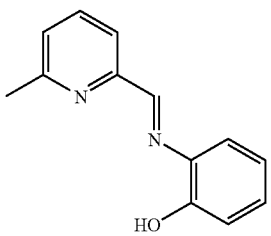

L17

$^1$H NMR (300 MHz, CDCl$_3$) δ (ppm): 2.63 (s, 3H), 6.75 (s, 1H), 6.95 (dt, J=2 Hz and J=0.5 Hz, 1H), 7.02 (dd, J=2 Hz and J=0.3 Hz, 1H), 7.26 (dt, J=2 Hz and J=0.5 Hz, 1H), 7.30 (d, J=2 Hz, 1H), 7.43 (dd, J=2 Hz and 0.4 Hz, 1H), 7.77 (t, J=2 Hz, 1H), 8.01 (d, J=2 Hz, 1H), 8.82 (s, 1H).

Synthesis of ligand 2-[2-(6-methylpyridyl)-methylimino]-4-nitro-phenol (L18)

Ligand L18 was prepared following the same procedure as that used to prepare ligand L1 except that 247 mg (1 mmol) of picoline-6-carboxaldehyde were used as reagent 1 and 321 mg (2 mmol) of 2-amino-4-phenol as reagent 2. 235 mg of ligand L18 were obtained as beige solid with a yield of 46%.

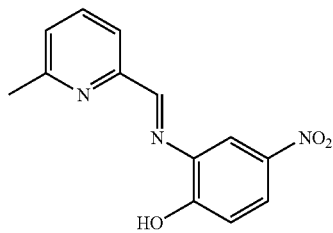

L18

¹H NMR (300 MHz, DMSO) δ (ppm): 2.55 (s, 3H), 7.09 (d, J=2.4 Hz, 1H), 7.41 (d, J=1.9 Hz, 1H), 7.86 (t, J=2 Hz, 1H), 8.05 (m, 3H), 8.68 (s, 1H), 11.0 (s, 1H).

Synthesis of ligand 2-[2-(6-methoxypyridyl)-methylimino]-4-nitro-phenol (L19)

Ligand L19 was prepared following the same procedure as that used to prepare ligand L1 except that 640 mg (1 mmol) of precursor E were used as reagent 1 and 482 mg (3 mmol) of 2-amino-4-nitrophenol as reagent 2. 747 mg of ligand L18 were obtained as orange brown solid with a yield of 71%.

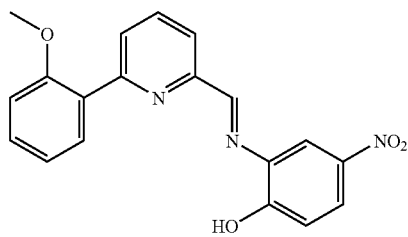

L19

¹H NMR (300 MHz, CD₂Cl₂) δ (ppm): 3.91 (s, 3H), 7.10 (q, J=2.3 Hz, 3H), 7.44 (m, 2H), 7.86 (dd, J=0.4 Hz and J=2.0 Hz, 1H), 7.93 (d, J=1.9 Hz, 1H), 8.02 (d, J=1.9 Hz, 1H), 8.12 (d, J=1.9 Hz, 1H), 8.25 (dd, J=0.6 Hz and J=2.0 Hz, 1H), 8.40 (d, J=0.6 Hz, 1H), 9.03 (s, 1H).

Synthesis of ligand 2-[2-(6-bromopyridyl)-methylimino]-4-nitro-phenol (L20)

Ligand L20 was prepared following the same procedure as that used to prepare ligand L1 except that 767 mg (4 mmol) of 6-bromo-2-pyridine carboxaldehyde were used as reagent 1 and 642 mg (4 mmol) of 2-amino-4-phenol as reagent 2. 1.20 g of ligand L20 were obtained as beige solid with a yield of 92%.

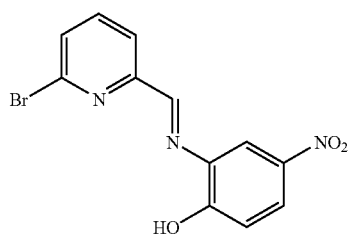

L20

¹H NMR (300 MHz, DMSO) δ (ppm): 7.12 (d, J=2.2 Hz, 1H), 7.83 (d, J=2.0 Hz, 1H), 7.98 (t, J=1.9 Hz, 1H), 8.08 (dd, J=2.2 Hz and J=0.7 Hz, 1H), 8.15 (d, J=0.7 Hz, 1H), 8.36 (d, J=1.9 Hz, 1H), 8.75 (s, 1H), 11.0 (s, 1H).

¹³C{¹H} NMR (75 MHz, DMSO) δ (ppm): 115.7, 116.0, 120.9, 120.8, 123.4, 129.6, 136.7, 139.4, 139.7, 140.5, 154.5, 157.0, 160.6.

Synthesis of ligand 2-[2-(6-(quinolin-8-yl)-pyridyl)-methylimino]-phenol (L21)

Ligand L21 was prepared following the same procedure as that used to prepare ligand L1 except that 469 mg (2 mmol) of precursor F were used as reagent 1 and 220 mg (2 mmol) of 2-aminophenol as reagent 2. 389 mg of ligand L21 were obtained as beige solid with a yield of 60%.

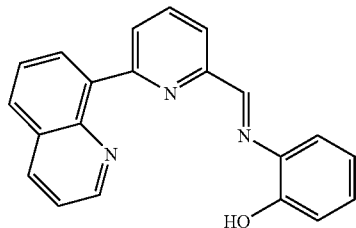

L21

¹H NMR (300 MHz, DMSO) δ (ppm): 6.95 (d, J=2.1 Hz, 1H), 7.10 (dd, J=2.0 Hz and 0.5 Hz, 1H), 7.38 (d, J=0.5 Hz, 1H), 7.61 (q, J=1.0 Hz, 1H), 7.77 (t, J=2.0 Hz, 1H), 8.06 (m, 2H), 8.20 (t, J=3.3 Hz, 2H), 8.39 (d, J=3.3 Hz, 1H), 8.45 (d, J=3.3 Hz, 1H), 8.80 (s, 1H), 8.97 (d, J=0.7 Hz, 1H), 9.58 (s, 1H).

Synthesis of ligand 2-[2-(6-(quinolin-8-yl)-pyridyl)-methylimino]-4-nitro-phenol (L22)

Ligand L22 was prepared following the same procedure as that, used to prepare ligand L1 except that 469 mg (2 mmol) of precursor F were used as reagent 1 and 321 mg (2 mmol) of 2-amino-4-nitrophenol as reagent 2. 538 mg of ligand L22 were obtained as beige solid with a yield of 73%.

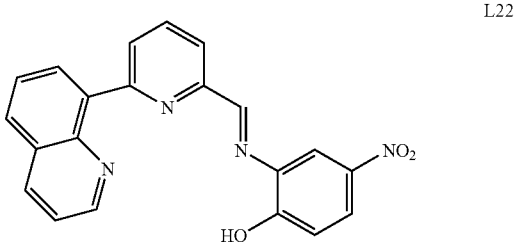 [SMILES: O=[N+]([O-])c1ccc(O)c(/N=C/c2cccc(-c3cccc4cccnc34)n2)c1]

L22

¹H NMR (300 MHz, DMSO) δ (ppm): 6.75 (d, J=2.1 Hz, 1H), 7.38 (dd, J=2.2 Hz and 0.7 Hz, 1H), 7.45 (d, J=0.7 Hz, 1H), 7.62 (dd, J=1.0 Hz and J=2.1 Hz, 1H), 7.79 (t, J=2.0 Hz, 1H), 7.97 (d, J=2.2 Hz, 1H), 8.10 (m, 2H), 8.22 (dd, J=1.8 Hz and J=0.3 Hz, 1H), 8.41 (dd, J=1.7 and J=0.2 Hz, 1H), 8.51 (dd, J=1.6 Hz and J=0.4 Hz, 1H), 8.96 (dd, J=1.0 Hz and J=0.4 Hz, 1H), 10.1 (s, 1H).

Synthesis of ligand 2-[2-(6-trifluoromethylpyridyl)-methylimino]-phenol (L23)

Ligand L23 was prepared following the same procedure as that used to prepare ligand L1 except that 628 mg (2.5 mmol)

of precursor G were used as reagent 1 and 276 mg (2.5 mmol) of 2-aminophenol as reagent 2. 612 mg of ligand L23 were obtained as brown solid with a yield of 72%.

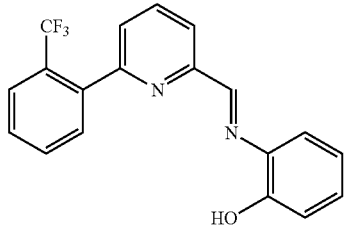

L23

Synthesis of ligand 2-[2-(6-trifluoromethylpyridyl)-methylimino]-4-nitro-phenol (L24)

Ligand L24 was prepared following the same procedure as that used to prepare ligand L1 except that 628 mg (2.5 mmol) of precursor G were used as reagent 1 and 401 mg (2.5 mmol) of 2-amino-4-nitrophenol as reagent 2. 658 mg of ligand L24 were obtained as beige solid with a yield of 68%.

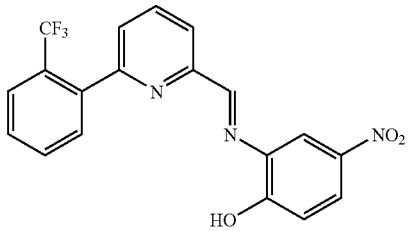

L24

$^1$H NMR (300 MHz, DMSO) δ (ppm): 7.10 (d, J=2.2 Hz, 1H), 7.67 (dt, J=1.9 Hz and 3.4 Hz, 3H), 7.79 (d, J=1.9 Hz, 1H), 7.90 (d, J=2.0 Hz, 1H), 8.08 (m, 3H), 8.37 (d, J=2.0 Hz, 1H), 8.75 (s, 1H), 11.00 (s, 1H).

Synthesis of ligand 2-[2-(6-(4-dibenzofuran))-methylimino]-phenol (L25)

Ligand L25 was prepared following the same procedure as that used to prepare ligand L1 except that 547 mg (2 mmol) of precursor H were used as reagent 1 and 220 mg (2 mmol) of 2-aminophenol as reagent 2. 597 mg of ligand L25 were obtained as pale orange solid with a yield of 82%.

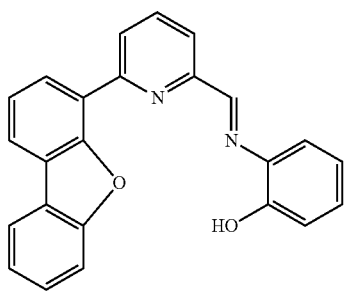

L25

$^1$H NMR (300 MHz, CD$_2$Cl$_2$) δ (ppm): 7.00 (t, J=1.8 Hz, 1H), 7.05 (d, J=2.0 Hz, 1H), 7.30 (t, J=1.8 Hz, 1H), 7.45 (t, J=1.8 Hz, 2H), 7.55 (q, J=1.9 Hz, 3H), 7.71 (d, J=2.0 Hz, 1H), 8.04 (m, 3H), 8.26 (d, J=1.9 Hz, 1H), 8.47 (d, J=1.8 Hz, 1H), 8.60 (d, J=2.0 Hz, 1H), 9.00 (s, 1H).

Synthesis of ligand 2-[2-(6-(4-dibenzofuran))-methylimino]-4-nitrophenol (L26)

Ligand L26 was prepared following the same procedure as that used to prepare ligand L1 except that 547 mg (2 mmol) of precursor H were used as reagent 1 and 321 mg (2 mmol) of 2-amino-4-nitrophenol as reagent 2. 603 mg of ligand L26 were obtained as beige orange solid with a yield of 74%.

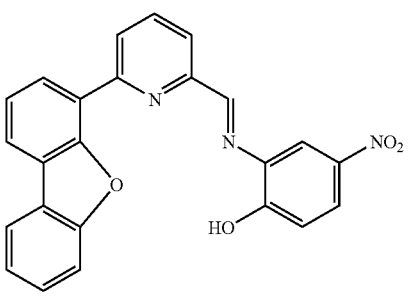

L26

$^1$H NMR (300 MHz, DMSO) δ (ppm): 6.76 (d, J=2.3 Hz, 1H), 7.47 (t, J=1.9 Hz, 1H), 7.59 (dt, J=1.7 Hz, 2H), 7.83 (d, J=2.0 Hz, 1H), 7.98 (dd, J=1.9 Hz, 1H), 8.16 (m, 5H), 8.40 (t, J=1.7 Hz, 2H), 8.58 (d, J=2.0 Hz, 1H), 8.90 (s, 1H).

Synthesis of ligand 2-[(2-pyridyl)-ethylimino]-phenol (L27)

450 µl (3 mmol) of 2-acetylpyridine (reagent 1), 331 mg (3 mmol) of 2-aminophenol (reagent 2) and a few mg of para toluene sulfonic acid were dissolved in 20 mL of dry toluene. The reaction mixture was stirred at a temperature of 140° C. for a period of time of 3 days. The solution was evaporated to dryness. After a chromatography on silica gel (heptane/AcOEt 8:2), 208 mg of ligand L27 were obtained as yellow solid with a yield of 33%.

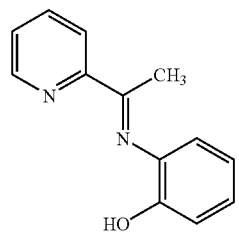

L27

$^1$H NMR (300 MHz, CD$_2$Cl$_2$) δ (ppm): 2.43 (s, 3H), 6.66 (t, J=1.9 Hz, 1H), 6.83 (dd, J=2.5 Hz and J=1.7 Hz, 1H), 7.06 (m, 1H), 7.22 (s, 1H), 7.45 (dt, J=2.3 Hz, 1H), 7.69 (m, 2H), 8.61 (dt, J=1.1 Hz, 1H), 10.01 (dt, J=1.8 Hz, 1H).

Synthesis of ligand 2-[(2-pyridyl)-ethylimino]-4-nitrophenol (L28)

Ligand L28 was prepared following the same procedure as that used to prepare ligand L27 except that 300 µL (2 mmol) of 2-acetylpyridine were used as reagent 1 and 321 mg (2 mmol) of 2-amino-4-nitrophenol as reagent 2. 156 mg of ligand L28 were obtained as dark yellow solid with a yield of 30%.

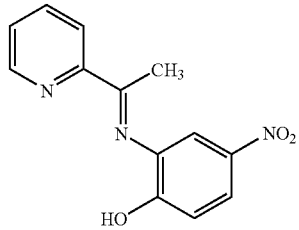

L28

$^1$H NMR (300 MHz, CD$_2$Cl$_2$) δ (ppm): 2.42 (s, 3H), 6.66 (t, J=1.7 Hz, 1H), 6.82 (t, J=2.0 Hz, 1H), 7.05 (m, 1H), 7.21 (s, 1H), 7.43 (dd, J=2.3 Hz, 1H), 7.67 (m, 2H), 8.60 (dd, J=1.2 Hz, 1H), 10.00 (dd, J=1.9 Hz, 1H).

Synthesis of ligand
2-[(2-pyridyl)-ethylimino]-1-propanol (L29)

561 µl (5 mmol) of 2-pyridinecarboxaldehyde (reagent 1) and 376 mg (5 mmol) of 3-amino-1-propanol (reagent 2) were dissolved in 10 mL of dry ethanol and the reaction mixture was stirred during 24 h. The solution was evaporated to dryness and the resulting oil was washed with pentane. Ligand L29 was obtained as yellow oil with a yield of 99%.

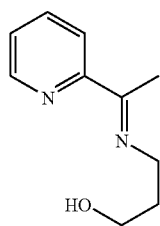

L29

$^1$H NMR (300 MHz, CDCl$_3$) δ (ppm): 2.00 (q, J=1.5 Hz, 2H), 2.37 (s, 3H), 3.69 (t, J=1.6 Hz, 2H), 3.92 (t, J=1.3 Hz, 2H), 7.28 (t, J=2.2, 1H), 7.69 (t, J=1.9 Hz, 1H), 7.93 (d, J=2.0, 1H), 8.58 (d, J=1.0 Hz, 1H).

III. Preparation of Metallic Complexes

Synthesis of Titanium (Ti(IV)) Complexes 198 mg (1 mmol) of ligand L1 was dissolved in 5 mL of THF and cooled to a temperature of −78° C. 1 mmol of n-butyl lithium (1.6M in hexane) was added drop-wise. The orange solution was stirred for 2 hours at room temperature. 1 mL (1 mmol) of TiCl$_4$ (1M in toluene) was dissolved in 5 mL of THF and cooled to a temperature of −78° C. The solution of the anionic ligand was added drop-wise to the solution of TiCl$_4$. The resulting solution was stirred overnight at room temperature. The mixture was evaporated to dryness and the complex was extracted with 10 mL of dry dichloromethane. The filtrate was evaporated and the residue was washed with 3 mL of diethyl ether, with 10 mL of pentane, and with another 10 mL of pentane. The resulting solid was dried under vacuum to afford 266 mg of complex A1 as brown-red powder with a yield of 76%.

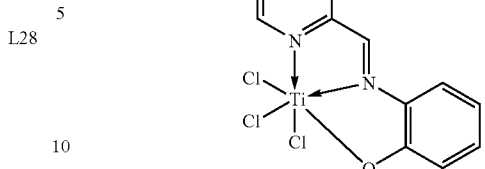

A1

Complexes A3, A4, A5, A6, A7, A8, A11, A12, A13, A14, A15, A16, A17, A18, A22, A23, A24, A25, A26, A27 and A29 were obtained from ligands L3, L4, L5, L6, L7, L8, L11, L12, L13, L14, L15, L16, L17, L18, L22, L23, L24, L25, L26, L27 and L29 following the same procedure as that used for obtaining complex A1 from ligand L1.

The yields are summarised in Table I.

TABLE I

| Ligand | Complex | Color of complex | Yield (%) |
|---|---|---|---|
| L3 | A3 | Dark red | 70 |
| L4 | A4 | brown | 60 |
| L5 | A5 | Dark red | 98 |
| L6 | A6 | Dark red | 99 |
| L7 | A7 | Dark red | 98 |
| L8 | A8 | Dark yellow | 76 |
| L11 | A11 | Dark red | 89 |
| L12 | A12 | Dark red | 67 |
| L13 | A13 | brown | 54 |
| L14 | A14 | brown | 61 |
| L15 | A15 | Dark yellow | 61 |
| L16 | A16 | beige | 82 |
| L17 | A17 | brown | 99 |
| L18 | A18 | Dark red | 99 |
| L22 | A22 | Dark yellow | 13 |
| L23 | A23 | brown | 84 |
| L24 | A24 | brown | 72 |
| L25 | A25 | red | 70 |
| L26 | A26 | Dark red | 46 |
| L27 | A27 | red | 21 |
| L29 | A29 | yellow | 46 |

Synthesis of Zirconium Zr(IV) Complexes 0.8 mmol of ligand L1 was dissolved in 5 mL of THF and cooled to a temperature of −78° C. 0.8 mmol of n-butyl lithium (1.6 M in hexane) were added drop-wise. The solution was stirred for 30 minutes at room temperature. 0.8 mmol of ZrCl$_4$ were dissolved in 5 mL of THF and cooled to a temperature of −78° C. The solution of the anionic ligand was added drop-wise to the solution of ZrCl$_4$. The resulting solution was stirred overnight under reflux at a temperature of 70° C. The mixture was concentrated to approximately 2 mL then 3 mL of diethyl ether and 10 mL of pentane were added. Solvents were filtered off and the solid was washed twice with pentane. The resulting solid was dried under vacuum to afford 140 mg of complex B1 as orange powder with a yield of 47%.

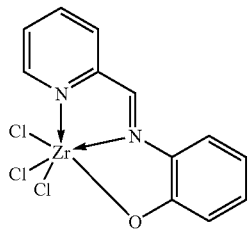

B1

Similarly, Zr(IV) complex B27 was obtained from ligand L27 as an orange powder with a yield of 77%.

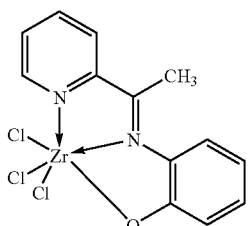

B27

Similarly, Zr(IV) complex B29 was obtained from ligand L29 as a yellow powder with a yield of 76%.

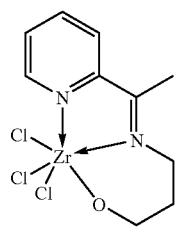

B29

Synthesis of Vanadium V(III) Complexes 150 mg (0.8 mmol) of ligand L1 were dissolved in 5 mL of THF and cooled to a temperature of −78° C. 0.8 mmol of n-butyl lithium (1.6 M in hexane) were added drop-wise. The solution was stirred for 30 minutes at room temperature. 0.8 mmol of $(THF)_3VCl_3$ were dissolved in 5 mL of THF and cooled to a temperature of −78° C. The solution of the anionic ligand was added drop-wise to the solution of $VCl_3$. The resulting solution was stirred overnight at room temperature. The mixture was evaporated to dryness and the complex was extracted with 10 mL of dry dichloromethane. The filtrate was concentrated to approximately 2 mL, and 10 mL of pentane were added. Solvents were filtered off and the solid was washed twice with pentane. The resulting solid was dried under vacuum to afford 233 mg of complex C1 as brown powder with a yield of 97%.

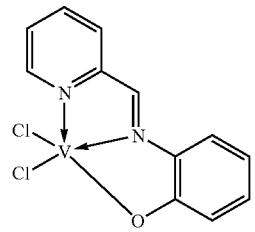

C1

Similarly, V(III) complex C27 was obtained from ligand L27 as a dark orange powder with a yield of 62%.

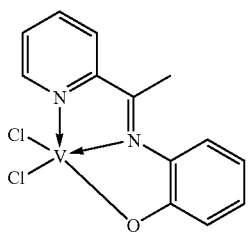

C27

Similarly, V(III) complex C29 was obtained from ligand L29 as a dark red powder with a yield of 99%.

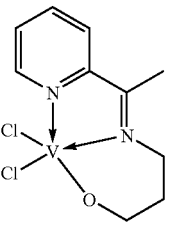

C29

Synthesis of Chromium Cr(III) Complexes 100 mg (0.26 mmol) of ligand L1 was dissolved in 5 mL of THF and cooled to a temperature of −15° C. 1 mmol of n-butyl lithium (1.6M in hexane) was added drop-wise. The solution was stirred for 30 minutes and added to a solution of 101 mg (0.26 mmol) of $(THF)_3CrCl_3$ dissolved in 5 mL of THF. The resulting solution was stirred overnight at room temperature. The mixture was concentrated to approximately 2 mL and 10 mL of pentane were added. Solvents were filtered off and the solid was washed twice with pentane. The resulting solid was dried under vacuum to afford complex D1 as a red powder with a yield of 93%.

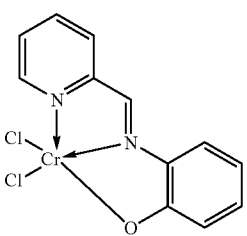

D1

Complexes D3, D4, D5, D6, D7, D8, D21, D22, D23, D24, D25, D26, D27 and D29 were obtained from ligands L3, L4, L5, L6, L7, L8, L21, L22, L23, L24, L25, L26, L27 and L29 following the same procedure as that used for obtaining complex D1 from ligand L1.

The yields are summarised in Table II.

TABLE II

| Ligand | Complex | Color of complex | Yield (%) |
|---|---|---|---|
| L3 | D3 | dark red | 99 |
| L4 | D4 | red | 89 |
| L5 | D5 | Dark red | 66 |
| L6 | D6 | purple | 99 |
| L7 | D7 | red | 99 |
| L8 | D8 | brown | 93 |
| L21 | D21 | black | 99 |
| L22 | D22 | red | 99 |
| L23 | D23 | Dark red | 75 |
| L24 | D24 | brown | 99 |
| L25 | D25 | red | 99 |
| L26 | D26 | brown | 99 |
| L27 | D27 | Dark yellow | 99 |
| L29 | D29 | Green | 99 |

Synthesis of fer Fe(III) Complexes 150 mg (0.8 mmol) of ligand L1 were dissolved in 5 mL of THF and cooled to a temperature of −15° C. 0.8 mmol of n-butyl lithium (C=1.6M in hexane) were added dropwise. The solution was stirred for 30 minutes and added to a solution of 127 mg (0.8 mmol) of anhydrous $FeCl_3$ dissolved in 5 mL of THF. The solution was stirred at room temperature overnight. The mixture was concentrated to approximately 2 mL and then 10 mL of pentane were added. Solvents were filtered off and the solid was washed twice with pentane. The resulting solid was dried under vacuum to afford complex E1 as black powder with a yield of 92%.

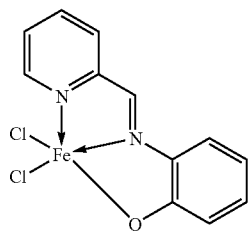

E1

IV. Polymerisation of Ethylene a. With Methylaluminoxane (MAO) as Activating Agent.

Ethylene polymerisation reactions were performed in a 20 mL stainless steel autoclave containing a glass insert, fitted with mechanical stirring, external thermocouple and pressure gauge and controlled by a computer. In a typical reaction run, the temperature was set at 50° C. or 80° C. and 4 mL of dry solvent (toluene or n-heptane) were introduced into the reactor under nitrogen flow. In an argon-filled glove box, about 4 mg (5 µmol) of the appropriate catalyst were weighted, activated with methylaluminoxane (MAO) activator (30% wt in toluene) in an appropriate amount to obtain a ratio [Al]:[M] of 2000 and diluted with toluene to obtain a final volume of 2 mL. 200 µL of the solution of activated catalyst were placed inside the reactor. The injection loop was rinsed with 800 µL of solvent. The ethylene pressure was raised to 15 bars and ethylene was fed continuously into the reactor. After 1 hour or an ethylene consumption of 12 mmol, the reactor was cooled down and depressurised, then the reaction was quenched with isopropanol and the solution analysed by gas chromatography. The gas chromatographic (GC) analysis of the reaction products was performed on a Trace GC apparatus with a Petrocol capillary column (methyl silicone, 100 m long, i.d. 0.25 mm and film thickness of 0.5 µm) working at a temperature of 35° C. for 15 min and then heating at a rate of 5° per minute up to a temperature of 250° C. The polymerisation results are displayed in Tables III for titanium complex and in Table IV for chromium complexes. GPC measurement could not be performed on all polymers because most polymers were not fully soluble in hot trichlorobenzene (140 to 180° C.) that was used as solvent.

TABLE III

| Run | Complex | solvent | T (° C.) | mPE (mg) | Activity (kg/mol/h) | DSC Tm (° C.) | DSC $\Delta H$ ($J \cdot g^{-1}$) |
|---|---|---|---|---|---|---|---|
| 1 | A1 | toluene | 80 | 174 | 341 | 133 | 146.8 |
| 2 | A1 | n-heptane | 80 | 644 | 1247 | 133 | 104.2 |
| 3 | A1 | toluene | 50 | 166 | 324 | 136 | 148.0 |
| 4 | A1 | n-heptane | 50 | 367 | 719 | 133 | 98.6 |
|  | A29 | n-heptane | 80 | 453 | 910 | * | * |

All reactions were performed with 0.5 µmol of catalyst dissolved in 5 mL of solvent and MAO was added to give a [Al]:[Ti] ratio of 2000.

Activities are expressed in kg of polyethylene per mol Ti per hour.

The obtained polymers were insoluble in hot trichlorobenzene and could not be caracterised by GPC.

TABLE IV

| Run | Complex | m PE (mg) | Activity (kg/mol/h) | DSC Tm (° C.) | DSC $\Delta H$ ($J \cdot g^{-1}$) |
|---|---|---|---|---|---|
| 5 | D1 | 135 | 271 | 129 | 195.2 |
| 6 | D3 | 129 | 252 | 131 | 169.5 |
| 7 | D4 | 54 | 104 | 130 | 205.3 |
| 8 | D5 | 162 | 312 | 127 | 193.1 |
| 9 | D6 | 117 | 227 | 128 | 209.2 |
| 10 | D7 | 158 | 320 | 130 | 181.9 |
| 11 | D8 | 139 | 281 | 131 | 175 |
| 12 | D1 | 77 | 154 | 129 | 210.5 |
| 13 | D3 | 119 | 235 | 130 | 156.9 |
| 14 | D4 | 79 | 152 | 129 | 178.0 |
| 15 | D5 | 80 | 152 | 128 | 217.4 |
| 16 | D6 | 75 | 153 | 130 | 218.3 |
| 17 | D7 | 76 | 154 | 131 | 183.2 |
| 18 | D8 | 91 | 190 | 131 | 120.6 |

All reactions were performed with 0.5 μmol of catalyst dissolved in 5 mL of solvent, and MAO was added to give a [Al]:[Cr] ratio of 2000. Runs 5 to 11 were performed in toluene and runs 12 to 18 were performed in n-heptane.

Activities are expressed in kg of polyethylene per mol Cr per hour.

$^{13}$C NMR analysis showed no short branches.

The obtained polymers were insoluble in hot trichlorobenzene and could not be caracterised by GPC.

b. With Tetra-Isobutyldialuminoxane (IBAO) as Activating Agent.

The procedure was the same as that described above with MAO except that the catalyst was activated with an appropriate amount of tetra-isobutyldialuminoxane ((iBu)$_2$-Al—O—Al-(iBu)$_2$) (10% wt in toluene). The polymerisation results are displayed in Table V.

TABLE V

| Run | Complex | m PE (mg) | Activity (kg/mol/h) |
|---|---|---|---|
| 19 | D1 | 293 | 588 |
| 20 | D3 | 380 | 728 |
| 21 | D4 | 271 | 534 |
| 22 | D5 | 309 | 631 |
| 23 | D6 | 348 | 690 |
| 24 | D7 | 335 | 701 |
| 25 | D8 | 208 | 380 |
| 26 | D1 | 299 | 600 |
| 27 | D3 | 398 | 761 |
| 28 | D4 | 267 | 526 |
| 29 | D5 | 528 | 1075 |
| 30 | D6 | 390 | 774 |
| 31 | D7 | 612 | 1293 |
| 32 | D8 | 269 | 492 |

All reactions were performed with 0.5 μmol of catalyst dissolved in 5 mL of toluene, at a temperature of 50° C., under an ethylene pressure of 15 bars. The amount of activating agent IBAO was adjusted to yield a ratio [Al]:[Cr] of 500. Runs 19 to 25 were performed in toluene and runs 26 to 32 were carried out in n-heptane.

Activities are expressed in kg of polyethylene per mol of Cr per hour.

When the catalyst components of the present invention are activated with IBAO, they exhibit a better activity than when activated with MAO. Without wishing to be bound by a theory, it is believed that IBAO, having a well defined structure, has a better activating efficiency than MAO that comes in oligomeric with residual trimethylaluminium.

The obtained polymers were insoluble in hot trichlorobenzene and could not be caracterised by GPC.

c. Polymerisation of Ethylene with Supported Catalysts.

Ethylene polymerisation reactions were carried out in a 130 ml stainless steel autoclave equipped with mechanical stirring and a stainless steel injection cylinder. In a typical reaction run, the reactor was first dried under nitrogen flow at 100° C. during 10 min. Then it was cooled down to the reaction temperature (50° C., 85° C. or 95° C.) and 35 ml of isobutane were introduced into the reactor with a syringe pump, followed by the comonomer if required. The pressure was adjusted to the desired value (14.8, 23.8, 29 or 33 bar) with ethylene. In an argon-filled glove box, TiBAl (10% wt in hexane), the appropriate supported catalyst (2 or 4% wt based on the total weight of the supported catalyst, on MAO impregnated silica) and n-hexane were placed into the injection cylinder. The valve was closed and the cylinder was connected to the reactor under nitrogen flow. The active catalyst mixture was then introduced into the reactor with 40 ml of isobutane. After 1 hour, the reactor was cooled down to room temperature and slowly depressurised, and the polymer was recovered. The comonomer, when present was hexene. The polymerisation results are displayed in Table VI.

TABLE VI

| Complex | Supported catalyst (mg) | Hexene (ml) | m PE (g) | Prod. (g/g·h) | Tm DSC (° C.) | SCB $^{13}$C NMR | Mw$^f$ kDa | Mn kDa | PDI |
|---|---|---|---|---|---|---|---|---|---|
| A1 (2 wt %) | 123.4 | / | 2.4 | 19.4 | 131.9 | 0 | Ins. | | |
| A1 (2 wt %) | 124.1 | 1.6 | 1.3 | 10.5 | 123.5 | 0.5 mol % (1.5 wt % C6) | Ins. | | |
| A1 (2 wt %) | 124.0 | / | 4.1 | 33.3$^a$ | 133.7 | <0.1% | Ins. | | |
| D7 (4 wt %) | 304.4 | / | 1.6 | 5.3$^b$ | / | <0.1% | Ins. | | |
| D7 (4 wt %) | 304.8 | 1.6 | 1.2 | 3.9 | 125.9 | 0.5 mol % (1.5 wt % C6) | 234.7 | 7.78 | 30.2 |
| B7 4 wt % | 300.9 | / | 2.2 | 14.6$^c$ | 128.9 | / | 538.6 | 10.69 | 50.4 |
| B1 4 wt % | 302.2 | / | 3.0 | 19.9$^d$ | / | / | / | | |
| B1 4 wt % | 300.8 | / | 2.2 | 7.3$^e$ | 129.2 | <0.1 mol % | 228.8 | 12.97 | 17.6 |
| C1 2 wt % | 300.8 | / | 1.2 | 3.9 | / | / | / | | |
| C1 2 wt % | 301.1 | / | 1.3 | 4.3 | / | / | / | | |

Figure 2:
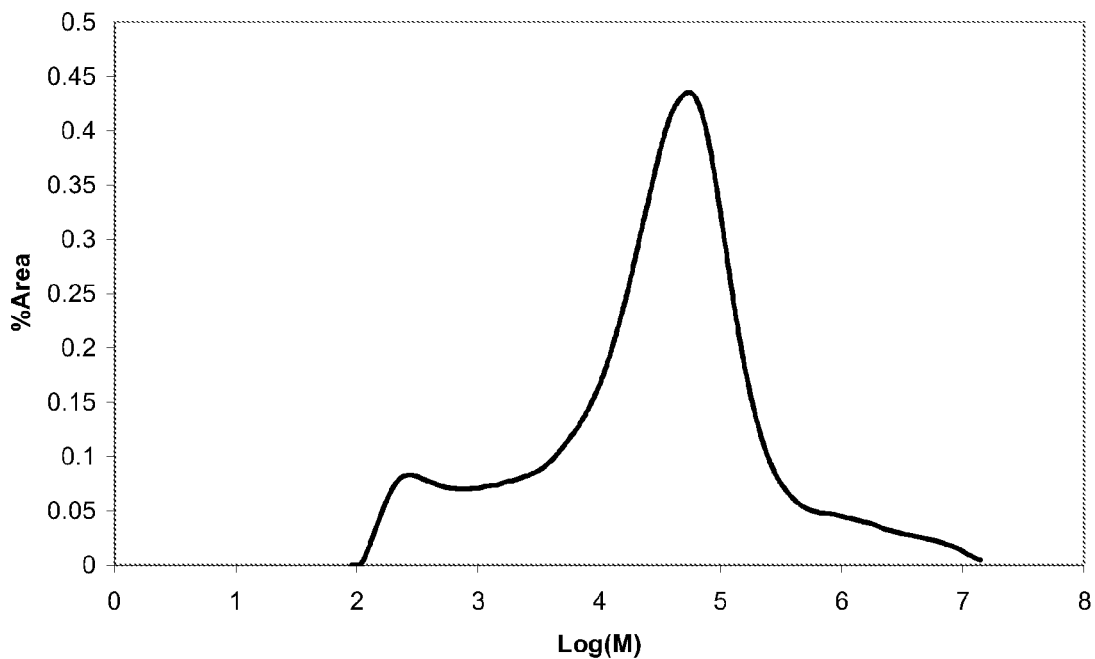
FIG. 2 represents the GPC curve of the polyethylene resin obtained with catalyst D1 activated with IBAO, with iC4 as solvent, at a temperature of 85° C., under an ethylene pressure of 24 bars and after a polymerisation time of 30 minutes.
Figure 3:
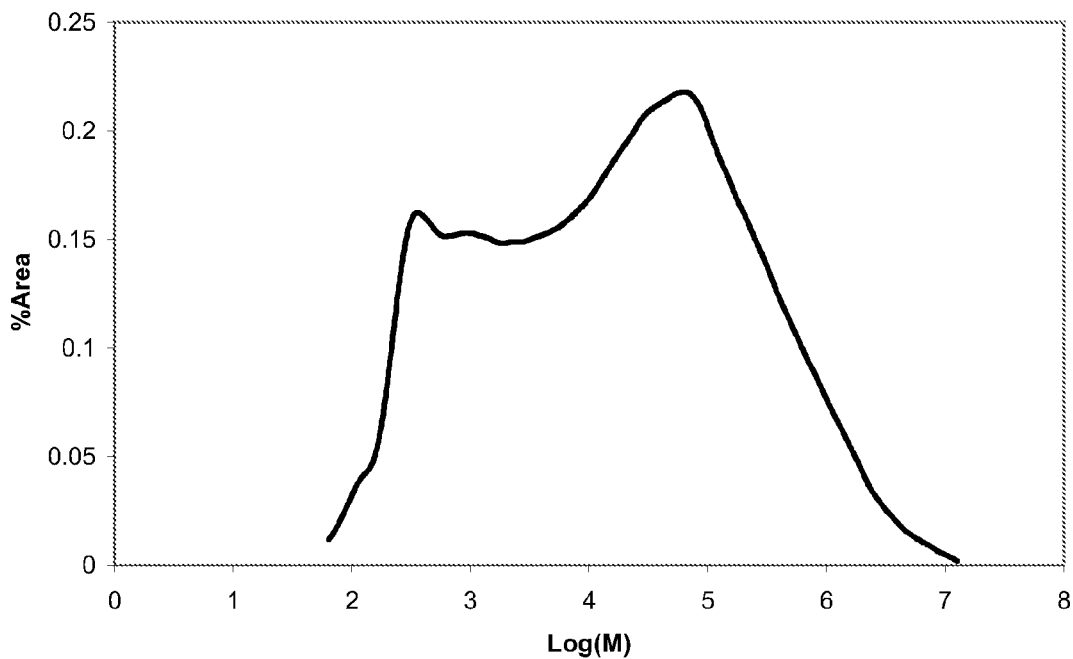
FIG. 3 represents the GPC curve of the polyethylene resin obtained with catalyst D7 activated with TiBAl, with iC4 as solvent and hexene as comonomer at a temperature of 85° C., under an ethylene pressure of 24 bars and after a polymerisation time of 60 minutes.

All reactions were performed in isobutane, at a polymerisation temperature of 85° C., under an ethylene pressure of 23.8 bars, with 25.6 mg of TiBAl as cocatalyst. Polymerisations were stopped after a period of time of 1 hour.
$^a$at 29 bar with 44.7 mg of tris-n-octyl-aluminium (TnOAl) instead of TlBAl.
$^b$at 50° C. under 14.8 bars of ethylene.
$^c$at 29 bar with 156 mg of IBAO instead of TiBAl; 30 min. instead of 1 h.
$^d$at 95° C. and 33 bar with 130 mg of IBAO instead of TiBAl; 30 min. instead of 1 h.
$^e$130 mg of IBAO instead of TiBAl.
$^f$Calculated for the curve between log(M) 3 to 8. For GPC curves, see FIGS. 1 to 3.
Ins. means insoluble.

d. Polymerisation of Ethylene in the Presence of Hydrogen as a Chain Transfer Agent.

The procedure was the same as that described above with MAO in paragraph IV.a except that the reactor was first pressurised with hydrogen, followed by ethylene to reach a final pressure of 19 bar. The polymerisation results are displayed in Table VII.

TABLE VII

| Run | Complex | [$H_2$]:[Ti] | m Polymer (mg) | Activity (kg/mol/h) | DSC Tm (° C.) | DSC $\Delta H$ ($J \cdot g^{-1}$) | GPC Mw | GPC Mn | GPC PDI |
|---|---|---|---|---|---|---|---|---|---|
| 33 | A1 | 0.06 | 78 | 152 | 129 | 160.4 | 278100 | 9430 | 29.5 |
| 34 | A1 | 0.11 | 61 | 119 | 128 | 179.8 | 201800 | 7160 | 28.2 |
| 35 | A1 | 0.17 | 69 | 135 | 128 | 173.7 | insoluble | | |
| 36 | A1 | 0.20 | 60 | 117 | 128 | 160.3 | 218000 | 8400 | 26.0 |

The reaction was performed with 0.5 μmol of catalyst dissolved in 5 mL of n-heptane, at a temperature 80° C. under a hydrogen-ethylene pressure of 19 bars and with MAO as activating agent. The amount of activating agent MAO was adjusted to yield a ratio [Al]:[Ti] of 2000.

Activities are expressed in kg polyethylene per mol of Ti per hour.

PDI is the polydispersity index defined as the ratio Mw/Mn of the weight average molecular weight Mw over the number average molecular weight Mn.

e. Polymerisation of Ethylene in the Presence of Diethyl Zinc as a Chain Transfer Agent.

The procedure was the same as that described above with MAO in paragraph IV.a except that an appropriate amount of diethyl zinc ($ZnEt_2$) was injected in the reactor before adding the catalyst. The polymerisation results are displayed in Table VIII.

an ethylene pressure of 19 bars and with MAO as activating agent. The amount of activating agent MAO was adjusted to yield a ratio [Al]:[Ti] of 2000.

Activities are expressed in kg polyethylene per mol of Ti per hour.

PDI is the polydispersity index defined as the ratio Mw/Mn of the weight average molecular weight Mw over the number average molecular weight Mn.

f. Polymerisation of Ethylene in the Presence of Methylaluminoxane (MAO) or Tetra-Isobutyldialuminoxane (IBAO) as Activating Agent.

Ethylene polymerisation reactions were performed in a 24 parallel reactors unit containing glass inserts of 50 ml and magnetic stirrers. In a typical reaction run, the catalyst was introduced into the glass insert. Then the activator (MAO or IBAO) and the solvent (22 to 24 ml of heptane) were added. The glass insert was sealed with a septum and placed into the 24 parallel reactors unit. While closing the reactor, the septum was pierced by a needle. The stirring was set at 1000 rpm and the temperature was set at 80° C. Then the pressure was raised to 22 bar of ethylene. These conditions were maintained

TABLE VIII

| Run | Complex | [$ZnEt_2$]:[Ti] | m Polymer (mg) | Activity (kg/mol/h) | DSC Tm (° C.) | DSC $\Delta H$ ($J \cdot g^{-1}$) | GPC Mw | GPC Mn | GPC PDI |
|---|---|---|---|---|---|---|---|---|---|
| 37 | A1 | 100 | 691 | 1349 | 135 | 177.2 | 410450 | 29220 | 14.0 |
| 38 | A1 | 250 | 342 | 668 | 134 | 190.8 | 155800 | 15460 | 10.1 |
| 39 | A1 | 500 | 317 | 619 | 132 | 216.3 | 86450 | 7190 | 12.0 |
| 40 | A1 | 1000 | 226 | 441 | 129 | 224.6 | 19410 | 3840 | 5.1 |

The reaction was performed with 0.5 μmol of catalyst dissolved in 5 mL of n-heptane, at a temperature 80° C. under during 20 min. The polymerisation results are displayed in Tables IX and X.

TABLE IX

| | Complex mg | Activator | PE ml | Activity g | Kg/mmol·h | HT-GPC Mw (Da) | HT-GPC Mn (Da) | HT-GPC PDI | DSC Tm (° C.) |
|---|---|---|---|---|---|---|---|---|---|
| B27 | 0.978 | MAO | 1.2 | 0.92 | 1.17 | / | | | |
| B27 | 0.98 | MAO | 1.2 | 0.87 | 1.10 | / | | | |
| C27 | 0.933 | MAO | 1.2 | 0.51 | 0.55 | / | | | |
| C27 | 1.367 | MAO | 1.2 | 0.59 | 0.44 | / | | | |
| A1 | 0.57 | MAO | 0.6 | 0.95 | 1.77 | / | | | |
| A1 | 0.57 | MAO | 0.6 | 1.05 | 1.96 | / | | | |
| A27 | 0.53 | MAO | 0.6 | 0.68 | 1.42 | / | | | |
| A27 | 0.53 | MAO | 0.6 | 0.68 | 1.42 | / | | | |
| D27 | 1.248 | IBAO | 2.6 | 0.253 | 0.21 | / | | | |
| D27 | 1.044 | IBAO | 2.6 | 0.214 | 0.21 | / | | | |
| C27 | 0.96 | IBAO | 2.6 | 0.104 | 0.11 | / | | | |
| C27 | 0.953 | IBAO | 2.6 | 0.129 | 0.14 | / | | | |
| A3 | 0.54 | MAO | 0.163 | 1.18 | 1.60 | insoluble | | | 135.4 |
| A3 | 0.54 | MAO | 0.163 | 1.17 | 1.58 | / | | | |

TABLE IX-continued

| Complex | Activator | PE mg | Activity ml | Kg/mmol·h | HT-GPC Mw (Da) | Mn (Da) | PDI | DSC Tm (°C.) |
|---|---|---|---|---|---|---|---|---|
| A15 | MAO | 0.522 | 0.163 | 0.73 | 1.46 | insoluble | | 137.1 |
| A15 | MAO | 0.522 | 0.163 | 0.68 | 1.36 | / | | |
| D6 | IBAO | 1.66 | 2.6 | 1.05 | 0.76 | / | | |
| D1 | IBAO | 1.44 | 2.6 | 0.70 | 0.47 | 275543 | 11545 | 23.9 | 130.9 |
| D1 | IBAO | 1.55 | 2.6 | 0.57 | 0.36 | 187629 | 8662 | 21.7 | 131.7 |
| D7 | IBAO | 1.57 | 2.6 | 0.66 | 0.45 | / | | |
| D7 | IBAO | 1.46 | 2.6 | 0.66 | 0.49 | / | | |

Figure 4:
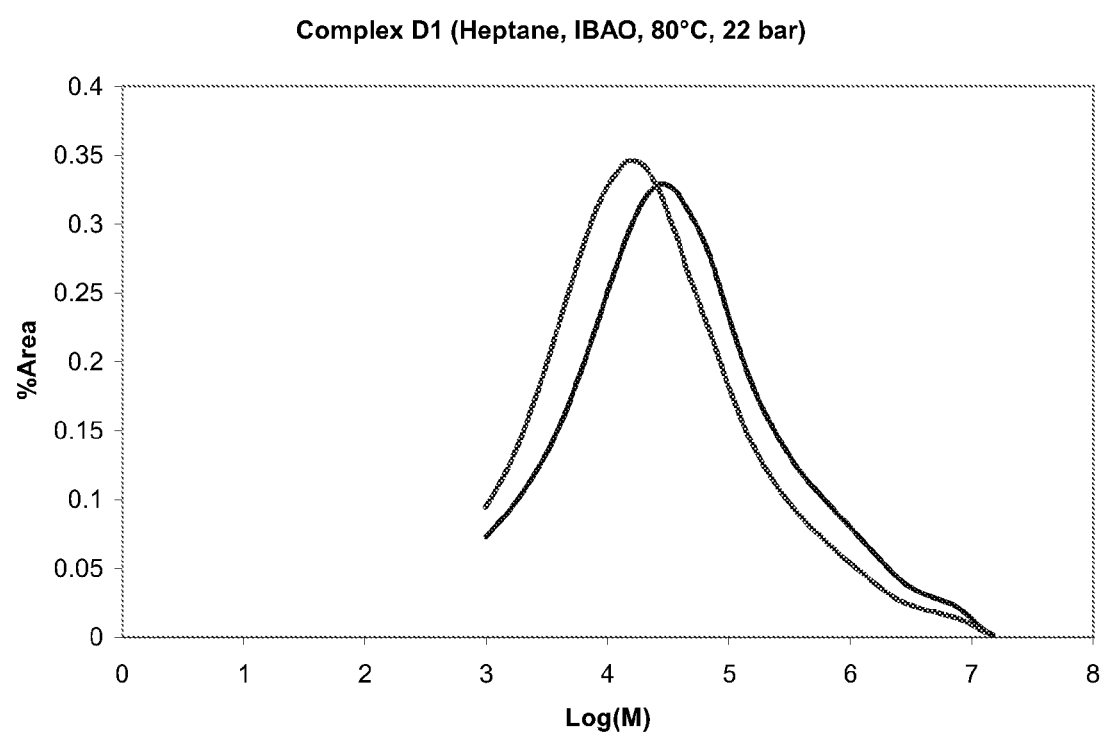
FIG. 4 represents the GPC curve of the polyethylene resin obtained with catalyst D1 activated with IBAO, with heptane as solvent, at a temperature of 85° C., under an ethylene pressure of 22 bars and after a polymerisation time of 30 minutes.

Conditions: Heptane 22-24 ml, 80° C., ethylene 22 bar, 20-30 min., 1000 rpm. For GPC curves, see FIG. 4.

TABLE X

| Complex | Activator | mg | ml | PE g | Activity Kg/mmol·h | HT-GPC | DSC Tm (°C.) |
|---|---|---|---|---|---|---|---|
| D1 | IBAO | 1.47 | 2.6 | 0.19 | 0.13 | / | / |
| D1 | IBAO | 1.23 | 2.5 | 0.18 | 0.14 | Insoluble | 134.1 |
| D6 | IBAO | 1.85 | 2.6 | 0.11 | 0.07 | / | / |

Conditions: Heptane 22 ml, 50° C., ethylene 15 bar, 20-30 min., 1000 rpm.

V. Copolymerisation Reactions a. Copolymerisation of Ethylene with Propylene.

The procedure was the same as that described above with MAO in paragraph IV.a except that the reaction was performed at 80° C., and that the reactor was first pressurised with propylene, followed by ethylene to a final pressure of 19 bar in order to obtain a mixture of 10% of propylene (molar fraction) in ethylene. The polymerisation results are displayed in Table XI.

TABLE XI

| Run | Complex | m Polymer (mg) | Activity (kg/mol/h) | DSC Tm (°C.) | ΔH (J·g$^{-1}$) | % Me branching |
|---|---|---|---|---|---|---|
| 41 | A1 | 293 | 572 | 126 | 127.4 | 2.2 |

The reaction was performed with 0.5 μmol of catalyst dissolved in 5 mL of n-heptane, at a temperature 80° C. under an ethylene pressure of 19 bars and with MAO as activating agent. The amount of activating agent MAO was adjusted to yield a ratio [Al]:[Ti] of 2000.

Activities are expressed in kg copolymer per mol of Ti per hour.

The obtained polymers were insoluble in hot trichlorobenzene and could not be caracterised by GPC.

b. Copolymerisation of Ethylene with Vinyltrimethylsilane.

The procedure was the same as that described above with MAO in paragraph IV.a except that an appropriate amount of vinyltrimethylsilane was injected in the reactor before adding the catalyst. The reaction was performed at 80° C. and to pressure of 19 bar. The polymerisation results are displayed in Table XII.

TABLE XII

| Run | Complex | [Silane]:[Ti] | m Polymer (mg) | Activity (kg/mol/h) |
|---|---|---|---|---|
| 42 | A1 | 500:1. | 610 | 1191 |
| 43 | A1 | 2000:1 | 740 | 1147 |

The reaction was performed with 0.5 μmol of catalyst dissolved in 5 mL of n-heptane, at a temperature 80° C. under an ethylene pressure of 19 bars and with MAO as activating agent. The amount of activating agent MAO was adjusted to yield a ratio [Al]:[Ti] of 2000.

Activities are expressed in kg copolymer per mol of Ti per hour.

Typical SiMe$_3$ bands were observed on the infrared spectra at 835; 855 and 1248 cm$^{-1}$.

The invention claimed is:

1. An active catalyst system comprising:
a metallic complex of formula I:

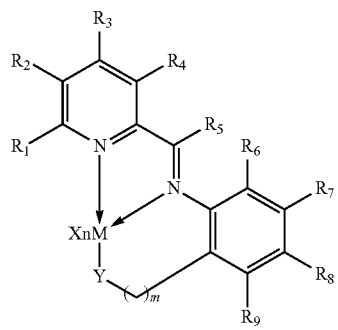

wherein $R_1$, $R_2$, $R_3$, $R_4$, $R_5$, $R_6$, $R_7$, $R_8$, $R_9$, are each independently selected from hydrogen, unsubstituted or substituted hydrocarbyl having from 1 to 20 carbon atoms, or inert functional group and two or more of those groups can themselves be linked together to form further ring or rings;

M is a metal Group 3 to 10 of the Periodic Table;

Y is O or NR*, R* being selected from alkyl or aryl having from 1 to 12 carbon atoms; each X is the same or different and is selected from halogen, substituted or unsubstituted hydrocarbyl having from 1 to 20 carbon atoms, substituted or unsubstituted aryloxy or alkoxy;

m is zero or an integer from 1 to 3; and (n+1) is the valence of M;

an activating agent selected from an aluminum or boron-containing complex; and optionally a scavenger, a transfer agent or combinations thereof.

2. The active catalyst system of claim 1, wherein m is zero and $R_2$, $R_3$, $R_4$, $R_5$, $R_6$, $R_9$ are the same and are hydrogen.

3. The active catalyst system of claim 1, wherein $R_1$, $R_7$, $R_8$ are each independently selected from hydrogen, substituted, unsubstituted hydrocarbyl having from 1 to 20 carbon atoms, halogen, nitro or cyano groups.

4. The active catalyst system of claim 1, wherein at least one of $R_1$, $R_7$ and $R_8$ is a compound other than hydrogen.

5. The active catalyst system of claim 1, wherein M is Ti, Cr, Zr or Fe.

6. The active catalyst system of claim 1, wherein X is Cl.

7. A method for preparing an active catalyst system comprising:
reacting a ligand of formula II

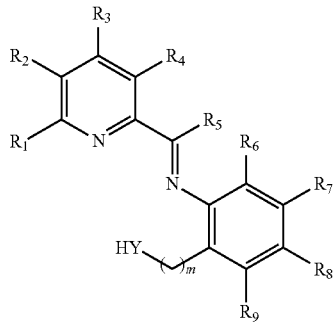

with a metallic salt in a solvent, wherein $R_1$, $R_2$, $R_3$, $R_4$, $R_5$, $R_6$, $R_7$, $R_8$, $R_9$, are each independently selected from hydrogen, unsubstituted or substituted hydrocarbyl having from 1 to 20 carbon atoms, or inert functional group and two or more of those groups can themselves be linked together to form further ring or rings;

M is a metal Group 3 to 10 of the Periodic Table;

Y is O or NR*, R* being selected from alkyl or aryl having from 1 to 12 carbon atoms;

each X is the same or different and is selected from halogen, substituted or unsubstituted hydrocarbyl having from 1 to 20 carbon atoms, substituted or unsubstituted aryloxy or alkoxy;

m is zero or an integer from 1 to 3; and (n+1) is the valence of M;

adding an activating agent exhibiting ionising action and selected from an aluminum or boron-containing complex or adding an activating support;

optionally adding or scavenger and/or a transfer agent; and retrieving an active oligomerisation or polymerisation catalyst system.

8. The method of claim 7, wherein the activating agent is a fluorinated activating support.

9. A method for oligomerising or homo- or co-polymerising ethylene and alpha-olefins comprising:
injecting the active catalyst system of claim 1 into a reactor;
injecting monomer and optional comonomer into the reactor either before, after or simultaneously with injection of the active catalyst system into the reactor;
maintaining the reactor under polymerisation conditions; and
retrieving the oligomers or polymer.

10. The method of claim 9, wherein the monomer and optional comonomer are selected from ethylene, propylene, or hexene.

* * * * *